United States Patent [19]
Chartrain et al.

[11] Patent Number: 5,534,422
[45] Date of Patent: Jul. 9, 1996

[54] BIOCONVERSION OF BETA KETO-ESTER TO (R) HYDROXYESTER

[75] Inventors: Michel Chartrain; Joseph D. Armstrong, III, both of Westfield, N.J.

[73] Assignee: Merck & Co., Inc., Rahway, N.J.

[21] Appl. No.: 447,163

[22] Filed: May 19, 1995

[51] Int. Cl.$^6$ ........................................ C12P 17/10
[52] U.S. Cl. .................. 435/118; 435/125; 435/126; 435/254.1; 435/911; 435/280
[58] Field of Search ..................................... 435/118, 125, 435/126, 280, 911, 254.1

[56] References Cited

U.S. PATENT DOCUMENTS

| | | | |
|---|---|---|---|
| 5,322,780 | 6/1994 | Kawashima et al. | 435/134 |
| 5,376,541 | 12/1994 | Kawashima et al. | 435/255.1 |
| 5,391,495 | 2/1995 | Patel et al. | 435/280 |
| 5,420,337 | 5/1995 | Patel et al. | 560/41 |

OTHER PUBLICATIONS

Program and Abstracts of the 33rd Interscience Conference on Antimicrobial Agents and Chemotherapy, 17–20 Oct. 1993, Abstract Nos. 898–906.

Nakagawa, et al., "In Vitro Activity of a New Carbapenem Antibiotic, BO-2727, with Potent Antipseudomonal Activity", Antimicrob. Agents and Chemo., Dec. 1993, pp. 2756–2759.

*Primary Examiner*—Herbert J. Lilling
*Attorney, Agent, or Firm*—Christine E. Carty; Jack L. Tribble

[57] ABSTRACT

A biotransformation process for the production of an intermediate used in the chemical synthesis of an antibiotic compound.

1 Claim, No Drawings

BIOCONVERSION OF BETA KETO-ESTER TO (R) HYDROXYESTER

BACKGROUND OF THE INVENTION

BO 2727 (a.k.a. L 739,428) of the formula [1R,5R,6S)-6-[(R)-1-hydroxyethyl]-2-{(3S,5S)-5-[(R)-1-hydroxy-3-N-methylaminopropyl]pyrrolidin-3-yl-thio}-1-methyl-1-carbapen-2-em-3-carboxylic acid is a new β-methyl-carbapenem that as proven to be a very effective broad spectrum antibiotic (Nakagawa et al., 1993). The synthesis of BO 2727 is a challenging one, because the molecule has a total of seven chiral centers. The mercaptopyrrolidine side chain of BO 2727 is derived from (R)-β-hydroxyester, which has three chiral centers. This (R)-β-hydroxyester is chemically synthesized from the β-ketoester precursor by chiral reduction.

As an alternative to chemical synthesis of the L-739,428, a bioconversion process employing *Mortierella alpina* strain MF5534 is presented. In this bioconversion process the β-ketoester is converted to the (R)-β-hydroxy ester. This bioconversion process yields to rapid process improvements and optimization of bioconversion conditions.

SUMMARY OF THE INVENTION

A biotransformation process for the production of a key intermediate used in the chemical synthesis of the antibiotic compound L-739,428 is presented. Fungal strain *Mortierella alpina* MF5534 (ATCC 8979) is employed for the bioconversion of the β-ketoester to the corresponding (R)-β-hydroxyester.

DETAILED DESCRIPTION OF THE INVENTION

A biotransformation process for the production of a key intermediate used in the chemical synthesis of the antibiotic compound L-739,428 is presented. Fungal strain *Mortierella alpina* MF5534 (ATCC 8979) is employed for the bioconversion of the β-ketoester to the corresponding (R)-β-hydroxyester.

The present invention is directed to a fermentation process which employs a readily prepared culture medium. Culture medium as used herein is defined as a mixture which supports the growth of fungal cells, which mixture contains ingredients such as peptone, soy peptone, and yeast extract powder. It should be understood that the precise amounts of ingredients provided above may be optimized, or modified so long as no new components are introduced. The key aspect of the medium is its ability to support growth of *Mortierella alpina* strain MF5534 and thereby the production of β-hydroxy-ester useful for pharmaceutical production.

The β-ketoester substrate of the present invention has the following structure:

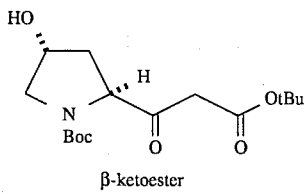

β-ketoester

The (R)-β-hydroxyester product of the present invention has the following structure:

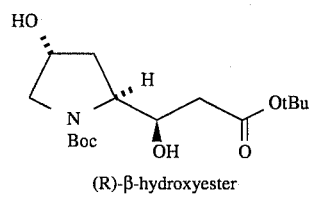

(R)-β-hydroxyester

It will be understood that by the expression "diastereomeric excess" or "de" is meant, the percent excess of one enantiomeric form over the other. If the ratio of the diastereomers is A: B, then DE=(A−B)/(A+B)*100.0.

A sample of *Mortierella alpina* strain MF5534 deposited under the Budapest Treaty in the American Type Culture Collection, 12301 Parklawn Drive, Rockville, Md. 20852, USA on Sep. 26, 1995 has been assigned accession number ATCC 74350.

The following examples demonstrate the use of *Mortierella alpina* strain MF5534 in the bioconversion of β-ketoester {[2S-[2α,4β]]-1-[(1, 1-dimethylethoxy)carbonyl]-4-hydroxy-β-oxo-2-pyrrolidine-propanoic acid 1,1-dimethylethyl ester} to (R)-β-hydroxyester {[2S-[2α(S*),4β]]-β,4-dihydroxy-1-[(1,1-dimethylethoxy)carbonyl]-2-pyrrolidinepropanoic acid 1,1-dimethylethyl ester}. The examples are not to be construed as a limitation on the scope of the invention.

EXAMPLE 1

Preparation of substrate

The substrate, {[2S-[2α, 4β]]-1-[(1,1-dimethylethoxy)carbonyl]-4-hydroxy-β-oxo-2-pyrrolidinepropanoic acid 1,1-dimethylethyl ester} β-ketoester may be prepared via a one-step synthesis, as outlined below:

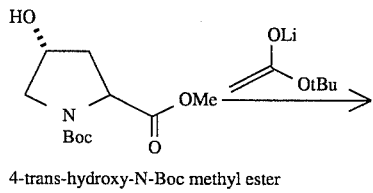

4-trans-hydroxy-N-Boc methyl ester

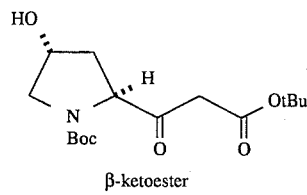

β-ketoester

EXAMPLE. 2

Shake flask fermentations

Cells preserved on YME agar slants at 4° C. were used to inoculate 250-ml flasks containing 50 ml of YME medium. YME medium contains yeast extract (4 g), malt extract (20 g) and glucose (4 g) per liter of water. The flasks were incubated aerobically at 28° C. on an orbital shaker operated at 220 rpm. After approximately 48 hours of incubation, an aliquot (2.5 ml) of culture was transferred to a 250 ml Erlenmeyer flask containing 50 ml of YME liquid medium.

The cultures were returned to the conditions described above. β-ketoester dissolved in ethanol was added to each flask after 48 hours of incubation such that the final concentration of ethanol was 1 ml/flask and the final concentration of β-ketoester was 1 g/l. The cultures were incubated for an additional 72 hours, under the conditions described above.

The contents of the flask were: mixed with an equal volume of ethyl acetate to form an emulsion. The emulsion was broken by centrifugation (10 minutes at 2500 rpm) in a Beckman bench top centrifuge. The ethyl acetate layer was separated and taken to dryness. The residues were resuspended in 2 ml of methanol and analyzed. Reverse phase HPLC analyses identifyed *Mortierella alpina* MF5534 as reducing the β-ketoester to the (R)-β-hydroxyester.

EXAMPLE 3

Shake flask fermentations

A frozen glycerol suspension of *M. alpina* MF5534 was used to inoculate a 250-mL flask containing 50 mL of KF medium. KF medium contains, per liter of water: Corn steep Liquor, 5 g; Tomato Paste, 40 g; Oatmeal Flour, 10 g; Glucose, 10 g; KF trace element solution, 10 mL. The pH of the medium is adjusted to pH 6.8 with NaOH. KF trace element solution contains the following (g/L): $FeSO_4 \cdot 7H_2O$, 1; $MnSO_4 \cdot 4H_2O$, 1; $CuCl_2 \cdot 2H_2O$, 0.025; $CaCl_2$, 0.1; $H_3BO_3$, 0.056; $(NH_4)_6Mo_7O_{24} \cdot 4H_2O$, 0.019; and $ZnSO_4 \cdot 7H_2O$, 0.2. The culture was incubated aerobically at 28° C. on a rotary shaker operated at 220 rpm for 72 hours. The inoculum (5%; v/v) was transferred to a 2 liter Erlenmeyer flask containing 500 mL of YME. After 48 hours, 10 mL of an ethanol solution containing 0.5 g of crude β-ketoester was added to each flask and the incubation was continued. Samples were taken daily, centrifuged, and the supernatants were analyzed by (HPLC) after a 1:10 dilution with the mobile phase. The concentration of (R)-β-hydroxyester was 550 mg/L after 170 hours of cultivation.

The flasks were harvested by centrifugation and the supernatant loaded on a 120 ml chromatography column containing 80 ml of the resin Amberchrom 161 (a nonionic, macroporous, polymeric resin, Supelco, Bellefonte, Pa.). The materials were eluted with a step gradient of methanol in water. Fractions were analyzed by HPLC for the presence of hydroxyester. The fraction containing the (R)-β-hydroxyester was dried and analyzed by NMR and by supercritical HPLC. NMR studies confirmed the structure of the (R)-β-hydroxyester, and supercritical HPLC indicated that the (R) enantiomer was produced with diasteriomeric excess of 98%.

EXAMPLE 4

Shake flask fermentations

A frozen glycerol suspension of *M. alpina* MF5534 was used to inoculate a 250-mL flask containing 50 mL of KF medium. The culture was incubated aerobically at 28° C. on a rotary shaker operated at 220 rpm for 72 hours. The inoculum (5%; v/v) was transferred to a 2 liter Erlenmeyer flask containing 500 mL of KF medium. The culture was incubated aerobically at 28° C. on a rotary shaker operated at 180 rpm for 72 hours. The inoculum (5%; v/v) was transferred again to a 2 liter Erlenmeyer flask containing 500 mL of medium similar in composition to YME except that glucose was replaced with another carbon source (fructose, galactose, sodium glutamate, glycerol and sucrose) at a 1:1 (w/w) concentration. The flasks were incubated for 48 hours under the conditions similar to those described in Example 3. After this incubation period, β-ketoester was added to each flask as described in Example 3.

The production of (R)-β-hydroxyester was monitored daily by reverse phase HPLC. Maximum β-hydroxyester titers of between about 650 and about 750 mg/l were achieved after 180 hours of incubation. The optical purity of the produced hydroxyester was measured as described in Example 3. All media tested supported the formation of (R)-β-hydroxyester with diastereomeric excess of at least 98%.

EXAMPLE 5

70 liter scale

Three frozen glycerol suspensions of *M. alpina* MF5534 were used to inoculate three 250-mL flasks containing 50 mL of KF medium. The cultures were incubated aerobically at 28° C. on a rotary shaker operated at 220 rpm for 48 hours. The inocula (5%; v/v) were pooled and transferred to three 2-liter Erlenmeyer flasks containing 500 mL (each) of KF medium. The cultures were incubated aerobically at 28° C. on a rotary shaker operated at 180 rpm for 72 hours. The three flasks were used to inoculate a 70-liter bioreactor containing 50 liters of YME. YME medium contains: yeast extract 4 g/L, malt extract 20 g/L, glucose 4 g/L, P2000 (Polypropyleneglycol P2000, Dow Chemical Co. Midland, Mich.), 1 mL/L.

The bioreactor was set at 220 rpm minimum agitation, 21 L/min aeration, 0.5 psi back pressure and dissolved oxygen tension was controlled by agitation at a minimum of 30%. When the culture reached late logarithmic growth as indicated by the on-line measured Oxygen Uptake Rate (OUR), crude β-ketoester (50 g) dissolved in 1 liter total of ethanol was added to the bioreactor to give a final concentration of 1 g/L. (R)-β-Hydroxyester production was monitored daily by reverse phase HPLC. A maximun (R)-β-hydroxyester tiler of 310 mg/L was achieved after 328 hours of incubation.

EXAMPLE 6

23 liter scale fermentation

A frozen glycerol suspension of *M. alpina* MF5534 was used to inoculate a 250-mL flask containing 50 mL of KF medium. The culture was incubated aerobically at 28° C. on a rotary shaker operated at 220 rpm for 48 hours. The inoculum (5%; v/v) was transferred to a 2 liter Erlenmeyer flask containing 500 mL of KF medium. The culture was incubated aerobically at 28° C. on a rotary shaker operated at 180 rpm for 72 hours. The entire culture was then used as inoculum for a 23-liter bioreactor containing 15 liters of A1 medium. The composition of medium A1 is as follows: yeast extract 12 g/L, malt extract 60 g/L, sucrose 12 g/L, P2000 1 mL/L. The bioreactor was set at 220 rpm minimum agitation, 6 L/min aeration, 0.6 psi back pressure and the dissolved oxygen tension was controlled by agitation at a minimum of 30%. When the culture reached late logarithmic growth as indicated by the on-line measured OUR, crude β-ketoester dissolved in 300 mL of ethanol was added to the bioreactor to give a final concentration of 1 g/l. (R)-β-Hydroxyester production was monitored daily by reverse phase HPLC and a maximum titer of 550 mg/l was achieved after 250 hours of incubation.

EXAMPLE 7

Analytical procedures

Reverse phase HPLC. The separation of hydroxyster and ketoester was achieved, employing a Rainin HPLC system comprised of: two analytical pumps, a UV detector, an autoinjector, and a Macintosh computer system. The column was a Zorbax RXC8 octyldiisopropylsilane bonded to the surface of 3- or 5-micron silica particles; (Macmod Analytical, Chadds Ford, Pa.) (4.6×250 mm). Separation was obtained by using a gradient of acetonitrile (0.1% $H_3PO_4$) and water (0.1% $H_3PO_4$) at a flow rate of 1.5 ml/minute. The gradient was 20/80 (v/v) acetonitile/water to 70/30 (v/v) over 10 minutes and held for twenty minutes. It was then requilibrated back to 20/80 (v/v) for seven minutes before performing the next injection. Detection was done at 200 nm, and (R)-/3-hydroxyester and β-ketoester eluted after 10.7 and 12.9 minutes, respectively.

SFC HPLC. Crystalline material was of >99.9:0.1 R:S diastereomeric ratio as determined by supercritical fluid chromatography with a diol silica column (EM Science) and a chiralcel (+) OD(H) column (Daicel Chem. Co.) in tandem (100 Bar $CO_2$; 1.0 mL/min; 8% $CH_3O$ H Modifier; 35° C.). The relative migrations of several compounds were:

| | |
|---|---|
| β-ketoester | 15.83 min |
| (R)-β-hydroxy ester | 18.78 min |
| (S)-β-hydroxy ester | 19.70 min |

EXAMPLE 8

NMR

The identification of the (S)-β-hydroxyester, (R)-β-hydroxyester and the β-ketoester was done by $^{13}C$ NMR. $^{13}C$ NMR spectra were recorded from $CD_3OD$ solutions at 75.5 MHz with $CD_3OD$ (49.1 ppm) as internal standard. For the (S)-β-hydroxyester the $^{13}C$ NMR resonances are listed below: δ172.9, 172.3,158.2, 156.7, 81.8, 81.6, 81.3, 71.9, 70.7, 70.3, 70.1, 61.4, 61.0, 57.0, 56.6, 40.9, 39.2, 37.1, 36.6, 28.8, 28.5. For the (R)-β-hydroxyester the $^{13}C$ NMR resonances are listed below: δ172.6, 172.3, 157.2, 156.7, 81.8, 81.3, 81.0, 70.8, 70.4, 69.2, 69.0, 61.8, 56.8, 56.2, 41.7, 41.1, 34.8, 34.4, 28.9, 28.5. For the β-ketoester the $^{13}C$ NMR resonances are listed below: δ204.8, 168.1,155.9, 83.0, 82.2, 81.7, 70.8, 70.0, 65.6, 65.3, 56.4, 56.0, 39.1, 38.3, 28.7, 28.6, 28.4.

What is claimed is:

1. A method of converting β-ketoester {[2S-[2α,4β]],-1-[(1,1-dimethylethoxy) carbonyl]-4-hydroxy-β-oxo-2-pyrrolidine-propanoic acid 1,1-dimethylethyl ester} to (R)-β-hydroxyester {[2S-[2α(S*),4β]]-β, 4-dihydroxy-1-[(1,1-dimethylethoxy)carbonyl]-2-pyrrolidinepropanoic acid 1,1-dimethylethyl ester} comprising:

(a) cultivating *Mortierella alpina* MF5534 (ATCC 74350)in a medium containing {[2S-[2α,4β]]-1-[(1,1-dimethylethoxy)carbonyl]-4-hydroxy-β-oxo-2-pyrrolidinepropanoic acid 1,1-dimethylethyl ester}; and (b) recovering the (R)-β-hydroxyester {[2S-[2α(S*), 4β]] -β,4-dihydroxy-1-[(1,1-dimethylethoxy)-carbonyl]-2-pyrrolidinepropanoic acid 1,1-dimethylethyl ester.

* * * * *